United States Patent
Stokes

(10) Patent No.: US 10,247,714 B2
(45) Date of Patent: Apr. 2, 2019

(54) FIELD ODOR SCREENING SYSTEM

(71) Applicant: Gregory E. Stokes, Marlborough, MA (US)

(72) Inventor: Gregory E. Stokes, Marlborough, MA (US)

( * ) Notice: Subject to any disclaimer, the term of this patent is extended or adjusted under 35 U.S.C. 154(b) by 0 days.

(21) Appl. No.: 15/455,301

(22) Filed: Mar. 10, 2017

(65) Prior Publication Data
US 2017/0261478 A1   Sep. 14, 2017

Related U.S. Application Data

(60) Provisional application No. 62/306,266, filed on Mar. 10, 2016.

(51) Int. Cl.
| | |
|---|---|
| *G01N 33/00* | (2006.01) |
| *A01K 15/02* | (2006.01) |
| *F24F 7/007* | (2006.01) |
| *F24F 9/00* | (2006.01) |

(52) U.S. Cl.
CPC ......... *G01N 33/0001* (2013.01); *A01K 15/02* (2013.01); *F24F 7/007* (2013.01); *G01N 33/0057* (2013.01); *F24F 9/00* (2013.01); *F24F 2221/44* (2013.01)

(58) Field of Classification Search
CPC ....................... G01N 33/0001; G01N 33/0057
See application file for complete search history.

(56) References Cited

U.S. PATENT DOCUMENTS

| | | | | |
|---|---|---|---|---|
| 6,334,365 B1* | 1/2002 | Linker | ................. | G01N 1/2214 |
| | | | | 73/864.71 |
| 9,303,446 B2* | 4/2016 | Fougeroux | ................ | E06B 5/00 |
| 2009/0077908 A1* | 3/2009 | Brasfield | ............ | G01N 33/0001 |
| | | | | 52/198 |
| 2012/0103060 A1* | 5/2012 | Brasfield | ............ | G01N 33/0004 |
| | | | | 73/23.34 |
| 2012/0111285 A1* | 5/2012 | Pearce | ................... | A01K 15/02 |
| | | | | 119/712 |
| 2014/0209192 A1* | 7/2014 | Lawrence | ................ | G01N 1/02 |
| | | | | 137/565.01 |
| 2015/0264892 A1* | 9/2015 | Nir | ......................... | A01K 15/02 |
| | | | | 119/795 |
| 2017/0098357 A1* | 4/2017 | Hoy | ....................... | G08B 15/02 |

FOREIGN PATENT DOCUMENTS

FR          3001803 A1 *   8/2014   ......... G01N 33/0001

* cited by examiner

*Primary Examiner* — Harshad R Patel
(74) *Attorney, Agent, or Firm* — Kevin M. Bamer

(57) ABSTRACT

A system that screens for particularly identified odors, such as those associated with explosive and other bomb-making materials, weapons and illegal drugs, includes an odor delivery unit with one or more fans that force air across the object being screened, such as a person. The airflow from the odor delivery unit passes over and across the object being screened creating an odor stream that passes through a partition that allows the odor stream to flow freely through it and simultaneously obscures a canine positioned on the other side of the partition from view by the person or object being screened.

2 Claims, 2 Drawing Sheets

FIELD ODOR SCREENING SYSTEM

CROSS REFERENCES TO RELATED APPLICATIONS

This application claims priority to U.S. Provisional Patent Application No. 62/306,266, filed on Mar. 10, 2016, the entire contents of which are hereby incorporated by reference.

FIELD

This invention relates generally to the field of odor detection by trained animals. Various embodiments improve the delivery and detection of targeted odors (e.g., explosives, illicit drugs, agricultural, chemical, etc.) by animals, such as dogs, trained to alert on such odors. Exemplary embodiments of the system enable screening of odors on persons, animals, or items in a safe and non-offensive manner.

BACKGROUND

There are many situations in which pedestrians or vehicles may be carrying materials which are prohibited from transport into or out of a designated area, such as, airports, sporting venues and high security facilities. The prohibited materials may include, for example, explosive materials and illegal drugs.

One method for screening for such materials is to individually search each pedestrian or vehicle for the prohibited material. Unfortunately, individual searching is extremely time-consuming and requires an inordinate number of searchers and an inordinate period of time.

Another method for screening for certain materials includes the use of detection systems or devices and instrumentalities. Such systems typically use ion mobility spectrometry (IMS) and are designed to detect certain chemicals, more specifically, particular airborne particles associated with the item for which detection is intended. As described in further detail below these types of systems suffer from various problems and prove inefficient and/or ineffective when compared to canine/dog sniffing detection methods.

The use of dogs as chemical detectors dates back to their use as hunting dogs several thousands of years ago. More recently, however, e.g., since World War II, dog-handler teams have been used extensively by the military to locate explosives. Civilian use of dogs first started with tracking individuals and locating drugs and other illegal contraband, including bombs and other explosive devices. Civilian use has now expanded to include the detection of many other items, such as, guns, pipeline leaks, gold ore and contraband food. In view of recent terrorist activities dogs are now being trained to also detect flammable and ignitable liquid residues to identify individuals that likely have recently handled materials potentially used in bomb manufacture. Such canines are commonly referred to as accelerant detector dogs and results of their odor detection in such situations have been found admissible in court in certain circumstances.

A general comparison between instrumental chemical detection devices and trained detector dogs demonstrates that for certain aspects instrumental detection may be preferable over canine detection. However, for many, if not most, aspects that are most important to the user, canine detection is the more preferable choice. For example, the selectivity of detector dogs is generally superior to instrumental methods. Dogs are able to generalize odorant signatures enabling the detection of target odors in the presence of additional significant distracting odors, without the false alerts commonly encountered with many instruments. Dogs use a highly sophisticated neural network to confirm explosives from the pattern of odor chemicals emanating from their representative parent molecule(s) rather than relying on the parent molecule required by most instrumental methods.

Another advantage of detector dogs over instrument methods is the overall speed of detection which is generally significantly faster in canine detection than instrumental methods. The detection of low vapor pressure explosives using typical IMS instruments requires trapping particles containing the adsorbed explosive vapors followed by transferring the particles into the detector for heating and analysis. This additional required step slows down detection times for instrument from seconds to minutes or even longer depending on the screening and swab time as well as the number of subjects/items to be tested in a given period of time. Dogs also utilize an extremely efficient sampling system and can often times go directly to the source of the odor and discover the explosive, unlike machines which are typically fixed.

Even though canine detection is preferable over machine detection for many reasons, bringing certain dogs into direct contact with a large number of pedestrians, or even vehicles, can present difficulties. For instance, some people are extremely fearful of dogs and other animals and, as a result, a person being screened may act irrationally and cause harm to a highly trained dog or its handler if the situation is not tightly controlled. Traveling among a large number of vehicles may also create the potential for harm to a highly trained dog or its handler. What is needed, therefore, is an accurate and reliable system to screen persons or other individual items, such as packages, baggage and other items, and obtain consistent positive identification of prohibited material while reducing false-positive identifications of prohibited material.

SUMMARY

An exemplary embodiment includes a screening system comprising an odor delivery unit forcing air in a controlled direction across an object being screened and generating an odor stream including odors emanating from the object being screened. The system of this embodiment also includes a canine trained to detect one or more odors in the odor stream, and an obscuring unit positioned in the odor stream and between the object being screened and the canine.

In accordance with a further aspect of the exemplary embodiment described above, the odor delivery unit includes one or more fans configured to direct airflow across the object being screened.

In accordance with a further aspect of the exemplary embodiment described above, at least one of the fans of the odor delivery unit is located above the object being screened and is configured to force air in a downward direction and towards the obscuring unit.

In accordance with a further aspect of the exemplary embodiment described above, the obscuring unit includes fixed slats that obstruct visibility between the object being screened and the canine.

In accordance with a further aspect of the exemplary embodiment described above, the obscuring unit includes rotatable louvers that obstruct visibility between the object being screened and the canine and can be adjusted to increase and/or decrease one or more of the visibility and a volume of the air being forced towards the canine.

According to a further exemplary embodiment a screening system is provided that comprises a fan unit forcing air in a controlled direction across an object being screened generating an odor stream including odors emanating from the object being screened, and an odor detection device configured to detect one or more predetermined odors in the odor stream. A system according to this further embodiment also includes an obscuring panel positioned in the odor stream and between the object being screened and the odor detection device.

In accordance with a further aspect of this additional exemplary embodiment, the odor delivery unit includes one or more fans configured to direct airflow across the object being screened.

In accordance with a further aspect of the additional exemplary embodiment described above, at least one of the fans of the odor delivery unit is located above the object being screened and is configured to force air in a downward direction and towards the obscuring unit.

In accordance with a further aspect of the additional exemplary embodiment described above, the obscuring unit includes fixed slats that obstruct visibility between the object being screened and the odor detection device.

In accordance with a further aspect of the additional exemplary embodiment described above, the obscuring unit includes rotatable louvers that obstruct visibility between the object being screened and said odor detection device and can be adjusted to increase and decrease one or more of the visibility and a volume of the air being forced towards the odor detection device.

BRIEF DESCRIPTION OF THE DRAWINGS

The aspects and features of various exemplary embodiments will be more apparent from the description of those exemplary embodiments taken with reference to the accompanying drawings, in which.

DESCRIPTION OF EXEMPLARY EMBODIMENTS

Figure 1:
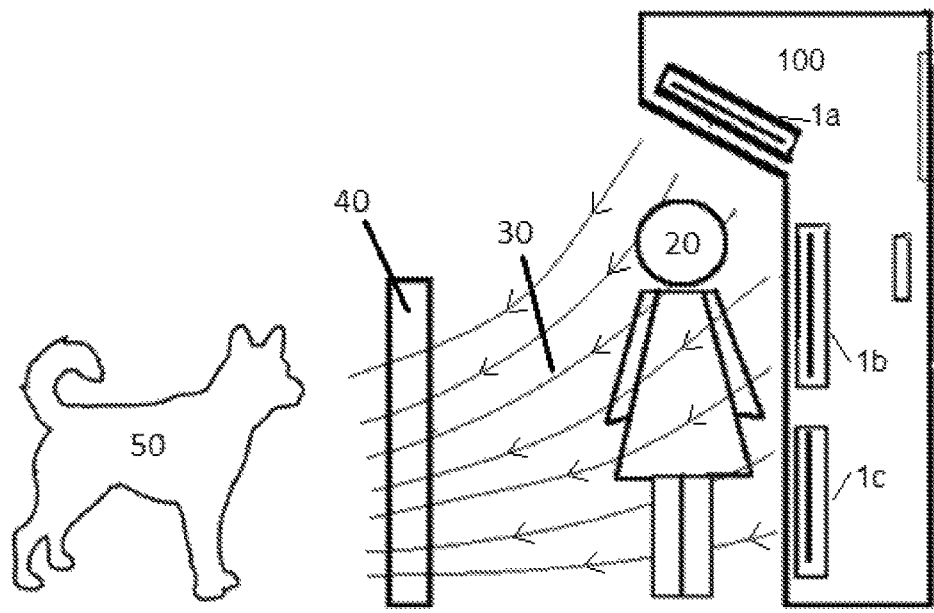
FIG. 1 is a schematic view of an exemplary system in accordance with the disclosure.

Referring to FIG. 1, an exemplary embodiment consistent with the present invention includes a system that permits fast, effective canine detection of specific odors for which the dog has been trained to detect, without requiring the animal to be in direct contact with the person or item being screened. More particularly, according to this embodiment odor delivery system (ODS) (100) is energized and fans 1a, 1b and 1c are individually calibrated by the system operator, either alone or using various known calibration tools, to a setting related to airflow measured in cubic feet per minute (cfm). The calibration takes ambient conditions into consideration. Such calibration enables, among other things, the unit to be employed in either indoor or outdoor environments and under various ambient conditions. One objective of the calibration procedure is to achieve a cfm level sufficient to 'push' odor particles being screened (30) to achieve the required 'odor stream.' However, in most situations the operator calibrates the system to a cfm level that prevents the rapid dispersion or 'spraying' of the odor particles.

The person, or other object, to be screened (20) stands, or is otherwise placed, on a designated location, such as "feet labels" on the floor/ground, and positioned as shown relative to the ODS. In accordance with the embodiment shown, the person's shoulders are made perpendicular to the front of the ODS (100). The feet labels are centered and perpendicular to the center of the ODS' fans (1a-1c) to ensure substantially equal amounts of air to pass by the person/object being screened on each side. This must be estimated much of the time by a handler experienced in the use of the system under variable conditions. The handler would then test and approve of the specific calibration using a test odor planted on a test subject prior to the system being employed.

The airflow, including particles to be detected, (30) is directed past the person/object being screened (20) forcing transport of the subject odor to be screened in the direction of arrows. The air and odor particulates pass through the Obscuring Permeable Partition (40) that obscures and physically separates the trained animal from the person/object being screened while allowing airflow to reach the trained animal positioned on the other side. The partition's louvers, e.g., 8'×4"×⅛" design, spaced one inch apart and angled 35 degrees downward toward the trained animal, making the person or object obscured to the animal as well.

The animal (50), such as a trained canine, screens for target odors as directed by its handler (e.g., explosives, drugs, agricultural products, etc.) and alerts as trained. The embodiment shown in FIG. 1 illustrates one system of what could be a series of co-located systems as dictated by screening throughput objectives and the amount of people/objects being screened.

Figure 2A:
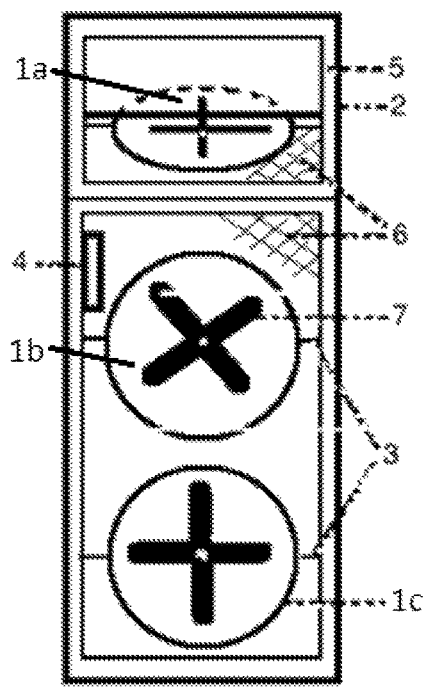
FIG. 2A is a front view of an odor delivery system (ODS) in accordance with the disclosure.
Figure 2B:
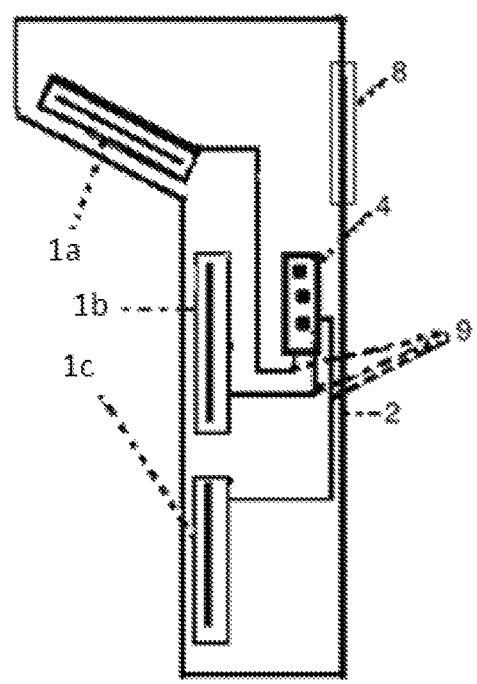
FIG. 2B is a side view of the odor delivery system (ODS) shown in FIG. 2A.

FIGS. 2A and 2B show the front and side views, respectively, of an odor delivery system (ODS) such as the one depicted in FIG. 1. Fans (1a-1c) are positioned to maximize the amount of odor stream produced in a downward direction across the body of the screened person/object and can be commercial fans, such as that are designed to work indoors or outdoors with blades (7) approximately 24-36 inches in diameter, with a minimum capability of about 2000 cfm.

Housing (2) in the embodiment shown in FIGS. 2A and 2B is a paneled cabinet made of aluminum sheets with a rear access door (not shown). Mounting Brackets (3) are fixed to the cabinet wall and are attached to and support fans 1a-1c. Modulation Unit (4), in accordance with the disclosed embodiment, includes three lighting rotary switches (not shown) corresponding to the three respective fans, 1a-1c, for example, 600-Watt Single-Pole, wired to respected fans mounted in an electrical housing. Housing Frame (5) in the present embodiment is two inch square aluminum tubing to which aluminum sheet is affixed.

In further reference to the exemplary embodiment of FIGS. 2A and 2B, mesh covering (6) comprises a flat sheet of aluminum mesh or screen having a mill finish, H14 temper cut into desired length, e.g., 4 feet, and width, e.g., 4 feet, with an overall thickness of approximately 0.060 inches.

Air Intake Mesh (8) is made of the same material as the mesh (6) covering the fan blades (7). Electrical Wiring (9)

electrically connects the modulation unit (4) to the fans 1a-1c and comprises 12-gauge wire rated for 20-amps of current.

Figure 3:
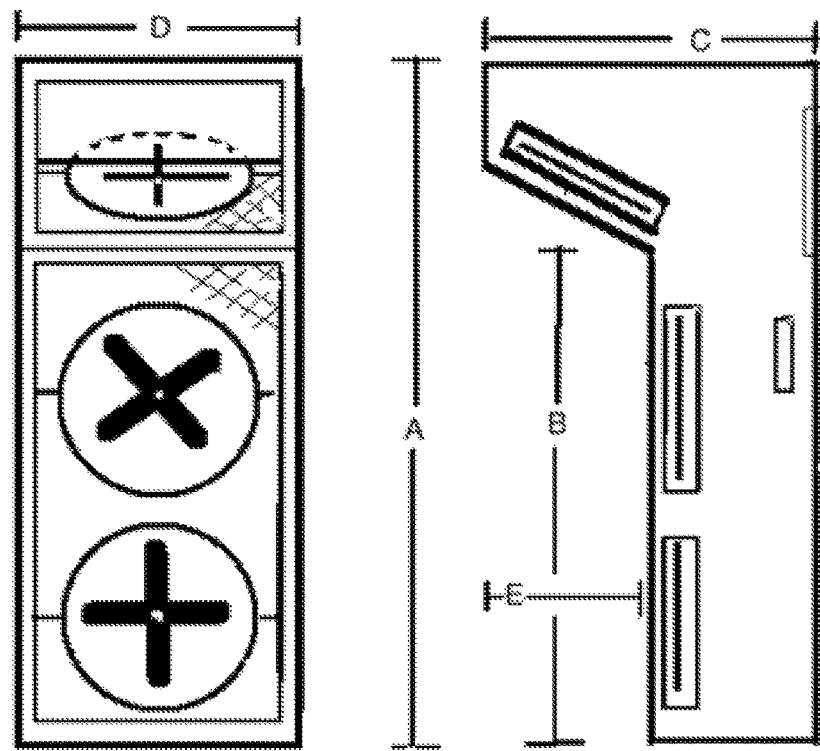
FIG. 3 shows the relative dimensions of various portions of the ODS as shown in FIGS. 2A and 2B.

FIG. 3 shows front and side views of the cabinet 100 with designations A-E depicting the relative size dimensions of the various sections of the cabinet. For example, height (A) indicates the overall height of the cabinet which, according to the embodiment shown, is approximately 9-10 feet and (C) represents the cabinet depth, which is approximately 5-7 feet. Dimension (B) depicts the height, and (E) represents the width, of the object chamber. The height (A) is approximately 7-8 feet tall to accommodate the height of most people and (E) is approximately 2-4 feet. The width of the cabinet, represented by (D) is approximately 4-6 feet. The dimensions indicated are exemplary and one of ordinary skill in the art would know that other dimensions can be used and are within the spirit and scope of the invention. For example, if the ODS is being used to detect odors on an object such as a suitcase, as opposed to a person as indicated in the present embodiment, the dimensions would be less than those provided above.

Figure 4:
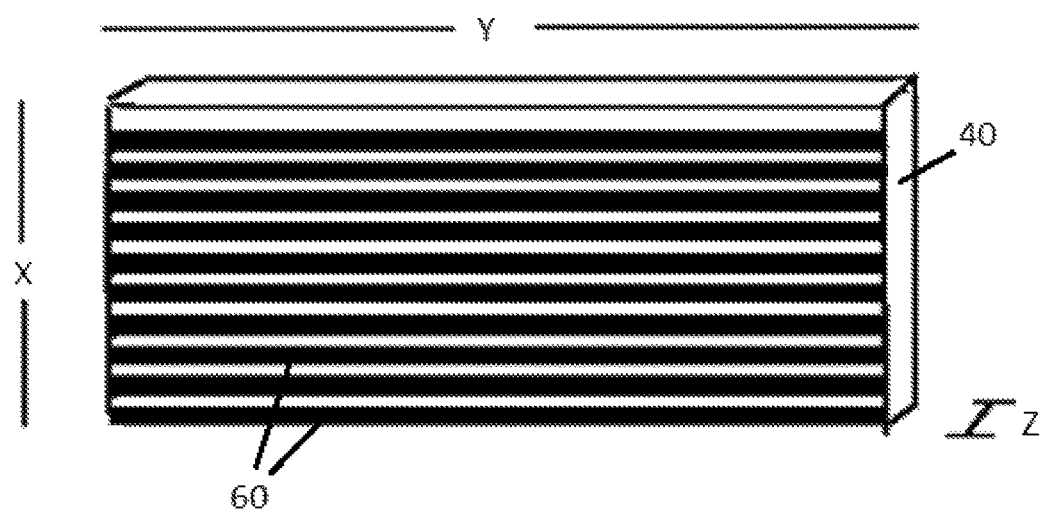
FIG. 4 is a perspective view of an exemplary obscuring permeable partition in accordance with the system shown in FIG. 1.

FIG. 4 illustrates a permeable barrier (e.g., 40 in FIG. 1) in accordance with one or more exemplary embodiments. According to the embodiment shown, barrier (40) includes slats or louvers (60) which obstruct the visibility of the animal, such as dog (50) in FIG. 1, from the perspective of the cabinet, and more specifically the person (20) being screened. Slats are fixed and louvers can be rotated to allow more or less air to pass through the barrier and conversely provide less or more visibility obstruction. For example, if the object being screened is a person it may be more desirable to provide increased visibility obstruction in order to limit the possible apprehension of the person being screened, e.g., if they are extremely afraid of dogs. On the other hand, of the object is a suitcase or some other inanimate object, it might be desirable to maximize the air flow and limit the visibility obstruction.

The dimensions of the exemplary permeable barrier (40) shown in FIG. 4 are indicated by the letters X, Y and Z. Height (X) is approximately 3-5 feet, for example, to provide a sufficient angle in order to obstruct the person's view of the dog. Length (Y), according to this embodiment, is approximately the same as dimension (D) provided in regard to FIG. 3 and width (Z) is approximately 6-12 inches to provide adequate free-standing stability to the barrier; however, it is possible that the barrier could be connected to a platform that also connects to the cabinet and, thus, can be thinner.

An exemplary embodiment of the invention operates as follows. The owner of a sports stadium employs the system to screen individuals for explosive odor before entering the venue. In accordance with the embodiment shown in FIG. 1, the person, or other object, to be screened (20) stands, or is otherwise placed, on a designated location, such as "feet labels" on the floor/ground, and positioned as shown relative to the ODS. The person's shoulders are made perpendicular to the front of the ODS (100). The feet labels are centered and perpendicular to the center of the ODS' fans (1a-1c) to ensure substantially equal amounts of air to pass by the person/object being screened on each side. The ODS sends odor past the person, captures odors in the airstream, and proceeds through the obscuring permeable barrier. On the opposite side of the barrier, the trained canine "sniffs" the air and alerts its handler of target odor should it be present. The person is detained for further investigation accordance with predetermined law enforcement/security operational procedure.

The foregoing description of the certain exemplary embodiments has been provided for the purpose of explaining the general principles and practical application, thereby enabling others skilled in the art to understand the disclosure for various embodiments and with various modifications as are suited to the particular use contemplated. This description is not necessarily intended to be exhaustive or to limit the disclosure to the exemplary embodiments disclosed. Any of the embodiments and/or elements disclosed herein may be combined with one another to form various additional embodiments not specifically disclosed. Accordingly, additional embodiments are possible and are intended to be encompassed within this specification and the scope of the appended claims. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present application, and are not intended to limit the structure of the exemplary embodiments of the present application to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. A screening system comprising:
   an odor delivery unit forcing air in a controlled direction across an object being screened generating an odor stream including odors emanating from said object being screened, wherein said odor delivery unit includes one or more fans configured to direct airflow across the object being screened and at least one of the fans is located above the object being screened and is configured to force air in a downward direction and towards;
   a canine trained to detect one or more odors in the odor stream;
   an obscuring unit positioned in the odor stream and between the object being screened and said canine, wherein said obscuring unit includes rotatable louvers that obstruct visibility between the object being screened and said canine and can be adjusted to increase and decrease one or more of said visibility and a volume of said air being forced towards said canine.

2. A screening system comprising:
   a fan unit forcing air in a controlled direction across an object being screened generating an odor stream including odors emanating from said object being screened wherein said fan unit includes one or more rotating fans configured to direct airflow across the object being screened and at least one of the fans of said fan unit is located above the object being screened and is configured to force air in a downward direction;
   an odor detection device configured to detect one or more predetermined odors in the odor stream;
   an obscuring panel positioned in the odor stream and between the object being screened and said odor detection device, wherein said obscuring panel includes rotatable louvers that obstruct visibility between the object being screened and said odor detection device and can be adjusted to increase and decrease one or more of said visibility and a volume of said air.

* * * * *